(12) United States Patent
Kasic et al.

(10) Patent No.: US 11,937,048 B2
(45) Date of Patent: Mar. 19, 2024

(54) INTEGRATED IMPLANTABLE HEARING DEVICE, MICROPHONE AND POWER UNIT

(71) Applicant: Cochlear Limited, Macquarie University (AU)

(72) Inventors: James Frank Kasic, Boulder, CO (US); James R. Easter, Lyons, CO (US)

(73) Assignee: Cochlear Limited, Macquarie University (AU)

( * ) Notice: Subject to any disclaimer, the term of this patent is extended or adjusted under 35 U.S.C. 154(b) by 980 days.

(21) Appl. No.: 16/658,268

(22) Filed: Oct. 21, 2019

(65) Prior Publication Data

US 2020/0114155 A1  Apr. 16, 2020

Related U.S. Application Data

(60) Continuation of application No. 15/063,680, filed on Mar. 8, 2016, now Pat. No. 10,449,376, which is a division of application No. 14/023,278, filed on Sep. 10, 2013, now Pat. No. 9,314,625, which is a division (Continued)

(51) Int. Cl.
*H04R 25/00* (2006.01)
*A61N 1/36* (2006.01)
*A61N 1/372* (2006.01)
*A61N 1/378* (2006.01)

(52) U.S. Cl.
CPC ....... *H04R 25/554* (2013.01); *A61N 1/37223* (2013.01); *A61N 1/3787* (2013.01); *H04R 25/606* (2013.01); *A61N 1/36038* (2017.08); *H04R 25/505* (2013.01);
(Continued)

(58) Field of Classification Search
CPC ............................ H04R 25/606; H04R 25/609
See application file for complete search history.

(56) References Cited

U.S. PATENT DOCUMENTS 6,067,474 A * 5/2000 Schulman .............. A61N 1/375
607/57
8,550,977 B2 * 10/2013 Kasic, II .............. H04R 25/554
600/25

(Continued)

*Primary Examiner* — Christine H Matthews
(74) *Attorney, Agent, or Firm* — Piloff Passino & Cosenza LLP; Martin J. Cosenza

(57) ABSTRACT

An implantable hearing unit is provided that includes an implantable microphone, a rechargeable power storage device and a speech signal processor. The hearing unit further includes a signal coupling device that is adapted for electrical interconnection to an implantable auditory stimulation device, which is operative to stimulate an auditory component of a patient. Such a stimulation device may include cochlear implants, brain stem stimulation systems, auditory nerve stimulation systems, and middle or inner ear transducer systems. The signal coupling device is operative to provide processed drive signals from the signal processor to the stimulation device as well provide power from the power storage device to operate the stimulation device. In one arrangement, the signal coupling device is a wireless coupling between first and second coils. In such an arrangement, the hearing unit may be utilized with an existing implanted stimulation device to make that device a fully implanted hearing system.

25 Claims, 6 Drawing Sheets

Related U.S. Application Data of application No. 11/356,434, filed on Feb. 16, 2006, now Pat. No. 8,550,977.

(60) Provisional application No. 60/653,415, filed on Feb. 16, 2005.

(52) U.S. Cl.
CPC .... *H04R 2225/021* (2013.01); *H04R 2225/31* (2013.01); *H04R 2225/67* (2013.01); *H04R 2420/07* (2013.01)

(56) References Cited

U.S. PATENT DOCUMENTS

| | | | |
|---|---|---|---|
| 10,449,376 B2 * | 10/2019 | Kasic | H04R 25/554 |
| 2001/0053871 A1 * | 12/2001 | Zilberman | H04R 25/606 |
| | | | 600/25 |

* cited by examiner

INTEGRATED IMPLANTABLE HEARING DEVICE, MICROPHONE AND POWER UNIT

CROSS REFERENCE TO RELATED APPLICATIONS

The present application is a continuation application of U.S. patent application Ser. No. 15/063,680, filed Mar. 8, 2016, which is a divisional application of U.S. patent application Ser. No. 14/023,278, filed Sep. 10, 2013, now U.S. Pat. No. 9,314,625, which is a divisional application of U.S. patent application Ser. No. 11/356,434, filed Feb. 16, 2006, now U.S. Pat. No. 8,550,977, which claims priority to U.S. Provisional Application No. 60/653,415, filed Feb. 16, 2005, the entire content of each of these applications being hereby incorporated by reference herein in their entirety.

FIELD OF THE INVENTION

The present invention relates to implanted hearing devices, and more particularly, to an implanted microphone and power unit assembly for use with an implantable stimulation device attached to a patient's auditory system.

BACKGROUND OF THE INVENTION

Implantable hearing devices stimulate internal components of the auditory system and are generally classified into one of two types, namely fully implantable hearing aids and semi-implantable hearing aids. In a fully implantable heating device, the entire device is implanted. In a semi-implantable hearing device, some of the components, typically the microphone, power supply, and speech signal processor, are externally worn, while the transducer/stimulator and key support functions are implanted within the auditory system. The externally worn portion communicates transcutaneosly with the implanted portion to provide audio signals that the implanted portion uses to stimulate to the auditory system.

By way of example, one type of implantable transducer includes an electromechanical transducer having a magnetic coil that drives a vibratory actuator. The actuator is positioned to interface with and stimulate the ossicular chain of the patient via physical engagement. (See e.g., U.S. Pat. No. 5,702,342). In this regard, one or more bones of the ossicular chain are made to mechanically vibrate, which causes the ossicular chain to stimulate the cochlea through its natural input, the so-called oval window.

Implanted hearing devices are typically used by individuals with significant loss of hearing function or damage to the auditory system. As a result, they differ in the manner by which the signal is processed and delivered to the patient. The processing step, known in the art as Speech Signal Processing ("SSP"), may include a number of steps such as amplification, frequency shaping, compression, etc. The steps in the SSP are determined by the design of the hearing device, while the particular internal values used in the steps are generated from prescriptive parameters determined by an audiologist. Once a speech processor receives an audio signal (e.g., from a Microphone) that is indicative of ambient acoustic signals, an drive signal produced and provided to an implanted stimulation device that stimulates the hearing impaired person's auditory system. The auditory stimulation may be done acoustically, mechanically, or electrically as a function of the type and severity of the hearing loss in the hearing impaired individual.

The type and/or severity of hearing loss may dictate what type of implantable hearing device may be beneficial to an impaired person. Heretofore, this has required that many impaired persons utilize semi-implantable hearing devices. Some surveys of current and potential hearing instrument wearers show that fully implantable or non-visible hearing devices have greater consumer acceptance. That is, there is some belief that fully implantable hearing devices may avoid stigmatizing cosmetics associated with semi-implantable devices.

SUMMARY OF THE INVENTION

The present invention is generally directed to the provision of an implantable hearing unit that includes an implantable microphone, a rechargeable power storage device, a speech signal processor (SSP). The hearing unit further includes a signal coupling device that is adapted for electrical interconnection to an implanted auditory stimulation device, which is operative to stimulate an auditory component of a patient. Such an implanted auditory stimulation device may include, without limitation, cochlear implants, brain stem stimulation systems, auditory nerve stimulation systems, and middle ear or inner ear transducer systems. Stated otherwise, the stimulation device may be any device that is operative to acoustically, electrically and/or mechanically stimulate an internal component of the auditory system of a patient.

As noted, the hearing unit incorporates the implantable microphone, the rechargeable power storage device and a signal processor. These components may be housed in a common implant housing, or these components may be separate implantable devices that are electrically connectable. The hearing unit may also incorporate additional components such as, but not limited to, memory devices, rectifying circuiting, etc. In any case, the implantable microphone is operative to transcutaneously receive sound and generate an output signal. The processor utilizes the output signal to generate a drive signal for use in actuating an implantable auditory stimulator device. As may be appreciated, the drive signal may be tailored to a particular stimulation device. The power storage device is operative to power the hearing unit as well as provide operating power to the auditory stimulation device via the signal coupling device. Further, the power storage device (e.g., one or more batteries) is rechargeable using transcutaneously received signals from an external source. Such signals may include electromagnetic signals (e.g., RF signals) as well as magnetic signals (e.g., inductive signals). Accordingly, the hearing unit may incorporate a receiver (e.g., coil or antenna) to receive such signals and/or a transmitter to transmit signals to an external receiver. To provide continuous operation for extended periods of time, the rechargeable power storage device may have a capacity of at least 20 mW/h, more preferably at least 50 mW/h and even more preferably at least 100 mW/h. However, it will be appreciated that use of the hearing unit with different stimulation devices may result in different power requirements. Accordingly, capacity of the power supply may be selected in accordance with needs of a particular system.

The signal coupling device is operative to provide processed drive signals from the signal processor to the implantable stimulation device. Furthermore, the signal coupling device is also operative to provide power from the power storage device to the implantable stimulation device. The use of the signal coupling device to electrically power and provide drive signals to an implanted stimulation device may allow for independent/separate subcutaneous placement of those components. This may simplify placement of the stimulation device relative to an auditory component of the patient. Further, the signal coupling device may allow for selective removal of the implantable hearing unit without disturbing the implantable stimulation device.

According to a first aspect of the present invention, an implantable hearing unit is provided that may be utilized with any of a variety of different implantable stimulation devices. In this first aspect, the signal coupling device is a wireless signal transmitter utilized to interconnect the hearing unit to the implantable stimulation device. That is, according to the first aspect a subcutaneously wireless link is established between two implantable devices, namely, an implanted hearing unit, which includes a microphone, power storage device and processor, and an implantable stimulation device. The wireless link between the implanted hearing unit and the implantable stimulation device electrically interconnects those devices for power transfer purposes as well as for transferring processed signals (e.g., drive signals) for use in auditory stimulation. In one arrangement, the wireless link comprises an inductive link. In such an arrangement, each device will typically include a coil for use in inductively transmitting/receiving signals (e.g., drive signals and/or power). Such signals may be modulated and/or demodulate in any appropriate manner including, without limitation, AM or FM modulation for analog signals as well as sigma-delta or pulse-width modulation for digital signals. FIG. 2B depicts a modulator 151 in black-box format that accomplishes the aforementioned modulation.

In one arrangement, use of the wireless signal coupling device with the implantable hearing unit may allow for retrofitting existing semi-implanted hearing instruments. Accordingly, such instruments may be converted from partially implanted hearing instruments into fully implanted hearing instruments. In this regard, the signal processor of the implantable hearing unit may be programmed to provide drive signals that are compatible with an existing implantable stimulation device (e.g., cochlear stimulation devices and/or middle ear devices). In such an application, removal of an implantable stimulation device already interconnected to a component of a patient's auditory system is not required to convert the device to a fully implantable hearing system. As will be appreciated, different implantable stimulation devices may be interconnected to auditory components in a manner that makes their removal undesirable and/or potentially damaging. For instance, removal of an electrode array of a cochlear implant would require surgery under general anesthesia and may cause damage to the cochlea thereby rendering the cochlea unable to utilize such an implant. Likewise, some middle ear transducers are affixed to one or more of the ossicle bones and may require removal of one or more ossicle bones, or cause damage to the ossicles, upon explanation. In either case, it is undesirable to remove implanted stimulation device.

However, many semi-implantable devices already include a wireless receiver (e.g., coil) that is operative to receive transcutaneous signals from an external speech processing unit. Accordingly, a wireless transmitter (e.g., an inductive coil) of the implantable hearing unit may be positioned relative to the wireless receiver of the implantable stimulation device upon implantation of the implantable hearing unit. This may effectively retrofit an existing semi-implantable hearing instrument such that it becomes a fully implantable hearing instrument, in a minimally invasive procedure, preferably under local anesthesia. To permit such positioning, the wireless transmitter may be interconnected to the hearing unit using a flexible connector.

In another arrangement of the present aspect, the wireless signal coupling device may be utilized with originally manufactured implantable hearing systems having two separate implantable portions. In this regard, a first portion of the implantable system may comprise the implantable stimulation device, which may be intended for long term or substantially permanent implantation. A second portion of implantable system may comprise the hearing unit that supports power, microphone and speech processing capabilities. The second portion of the implantable system may be conveniently located such that is more easily accessible for replacement and/or upgrade. Preferably, the second portion may be accessible under local anesthesia. Likewise, the wireless signal coupling device may permit the first portion of the implantable system to be located relative to a given auditory component with less concern about future access. In any case, the two-portion fully implantable system that utilizes a wireless signal coupling device may permit easy access and servicing of the hearing unit without disturbing the stimulation device; thus, the difficulty and risk of disturbing the delicate structures of the middle or inner ear may be avoided.

According to another aspect of the present invention, an implantable module or hearing unit, which provides power, microphone and signal processing functions, is interconnected to an implantable cochlear stimulation device by a conductive signal coupling device. Such a conductive signal coupling device may include a flexible communications wire. Such a flexible communications wire may facilitate positioning of the hearing unit of a stimulation device. Importantly, the conductive signal coupling device includes a detachable connector that allows for selective disconnecting of the implantable hearing unit and the implantable cochlear stimulation device. As will be appreciated, the cochlear stimulation device will include an electrode array that is adapted for insertion into the cochlea of the patient. Once inserted into the cochlea, it is desirable that disturbance of the electrode array be minimized. Accordingly, use of the selectively detachable connector permits removal of the implantable hearing unit without removal or disturbance of the implantable cochlear stimulation device.

Any appropriate conductive signal coupling device may be utilized. Generally, the conductive signal coupling device will include at least a first communications wire that extends from one of the implantable hearing unit or the implantable stimulation device. Such a communications wire extending from one of the implantable devices may plug into the other device, or, communications wires from each device may be connected by a connector disposed between the devices. The connector may be of any appropriate type. In one embodiment, a pacemaker-style, or "IS-1" connector is utilized. However, it will be appreciated that any connector that is operative for use in an implantable environment may be utilized. While any appropriate communications wire(s) may be used to interconnect the implantable hearing unit and the implantable stimulation device, it may be desirable to reduce the number of conductors (e.g., leads) interconnecting the two implantable devices to simplify the mechanical connector. For instance, in one embodiment a two conductor communications wire may be utilized.

In order to transmit appropriate levels of data between the implantable hearing unit and the implantable stimulation device, especially when using a reduced number of conductors, modulation and demodulation of the signals may be required. As will be appreciated, some implantable stimulation devices utilized multiple channels and or electrodes (e.g., 24 electrodes) for stimulation purposes. In this regard, it may be necessary to convey a relatively large quantity of drive signal information for use in stimulating patient auditory component. Compression, modulation and/or demodulation of signals sent across communications wire may be required. Examples of such modulation in the modulation schemes include, without limitation, Frequency Division Multiplexing (FDM) and Time division Multiplexing (TDM).

According to another aspect of the present invention, a method is provided for wirelessly interconnecting an implantable hearing unit with an implantable stimulation device. The method includes the steps of positioning an implantable hearing unit relative to an implantable stimulation device. Once positioned, a wireless signal coupler generates a wireless link that electrically interconnects the hearing unit to the stimulation device to permit the transmission of power and drive signals therebetween. Accordingly, once the implantable hearing unit is wirelessly interconnected to the implantable stimulation device, the hearing unit may generate drive signals and provide such drive signals to the stimulation device via a subcutaneous wireless link. In conjunction with providing drive signals, the hearing unit may also provide power over to the wireless link. The provided power may allow the stimulation device to operate and utilizes the drive signal to stimulate an auditory component of a patient.

The step of positioning may entail positioning a wireless transmitter associated with the implantable hearing unit relative to a wireless receiver associated with the implantable stimulator. For instance, the wireless transmitter and wireless receiver may be disposed in a substantially face-to-face relationship such that an inductive coupling may exist therebetween. However, it will be appreciated that the wireless transmitter and wireless receiver need not be in direct contact and may be separated. What is important is that the wireless transmitter and wireless receiver are operative to subcutaneously exchange signals.

The step of positioning may be performed during a surgical procedure wherein one or both of the implantable hearing unit and implantable stimulation device are implanted. Alternatively, step the positioning may be performed where the implantable hearing unit is implanted relative to a previously implanted stimulation device.

According to another aspect of the present invention, a method for electrically interconnecting first and second separate modules of a fully implantable cochlear hearing instrument is provided. The method includes positioning a cochlear stimulation device (e.g., a first module) relative to the first subcutaneous location on the body of a patient (e.g., relative to the cochlea). The method further includes positioning an implantable hearing unit (e.g., a second module) relative to a second subcutaneous location on the body of a patient. Once the cochlear stimulation device and the implantable hearing unit are positioned relative to the first and second subcutaneous locations, a signal coupling device, such as a communications conductor or wire, is subcutaneously routed between the implanted hearing unit and implanted cochlear stimulation device. The communications wire may releasably connect the implantable hearing unit and stimulation device to permit removal of one module without requiring removal of the other module.

According to another aspect of the present invention, a method for use with an implantable auditory stimulation device is provided. The method includes generating a drive signal at a first subcutaneous implant module where the drive signal is operative to actuate an implantable auditory stimulation device. The method further includes wirelessly transmitting the drive signal from the first subcutaneous implant module to a second subcutaneous implant module associated with an implantable auditory stimulation device. Accordingly, the method may further include actuating the auditory stimulation device according to the drive signal. Generating the drive signal may further include receiving sound at a subcutaneous microphone and generating an output associated with that sound. This microphone output may then be processed to generate the drive signal.

Wirelessly transmitting the drive signal may include generating an inductive coupling between the first module and the second module wherein magnetic signals may be exchanged therebetween or creating an RF link between these modules such that electromagnetic signals may be exchanged therebetween. In any case, the method may further include wirelessly transmitting power from a power supply associated with the first implant module to the second implant module. Preferably, this power supply should be sufficient to run the second implant module and an associated auditory stimulation device associated therewith. In one arrangement, wirelessly transmitting power may include transmitting power sufficient to operate the second module and the auditory stimulation device for at least eight hours. In a further arrangement, the transmitted power may be sufficient to operate the device for at least 12 hours and, in a yet further arrangement, at least 16 hours.

In order to provide power for the second implant module, the method may further include recharging the power supply associated with the first implant module. Such recharging may occur periodically and may entail the transcutaneous receipt of at least one of electromagnetic signals and magnetic signals. In any case, the received signals are utilized to charge the power supply. Accordingly, it will be appreciated that, in order to provide a continuous power supply for a predetermined period of time, it may further include the selection of a power supply having a predetermined capacity, wherein that capacity allows for a continuous expected discharge over the period of time.

The drive signals that are generated by the first implant module may include signals that are specific to a given implantable stimulation device. For instance, such signals may include signals that may be utilized for actuating an intracochlear electrode, a middle ear transducer, an inner transducer, etc.

DETAILED DESCRIPTION OF THE INVENTION

Reference will now be made to the accompanying drawings, which at least assist in illustrating the various pertinent features of the present invention. In this regard, the following description of a hearing instrument is presented for purposes of illustration and description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
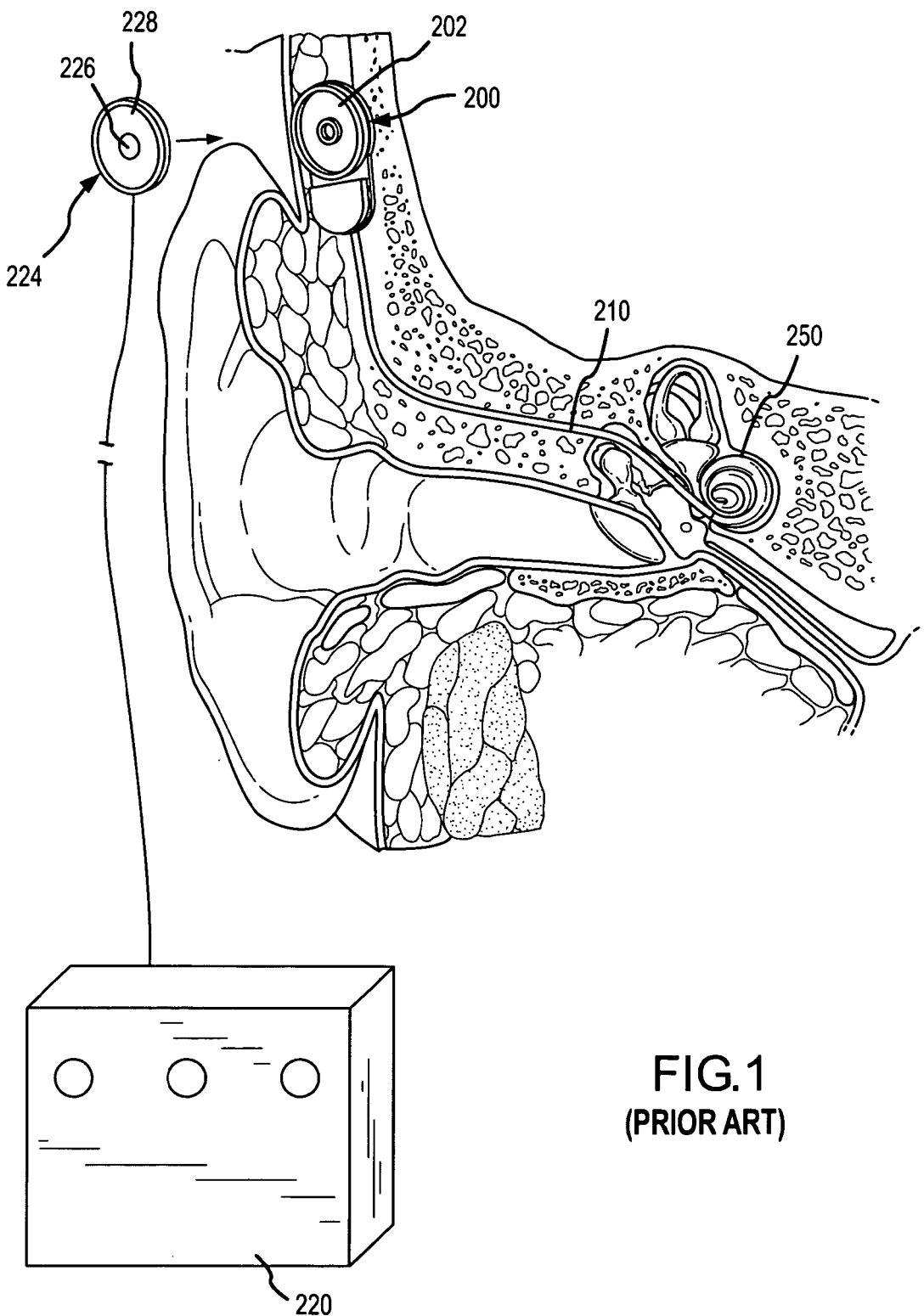
FIG. 1 illustrates a semi-implantable cochlear implant.
Figure 2A:
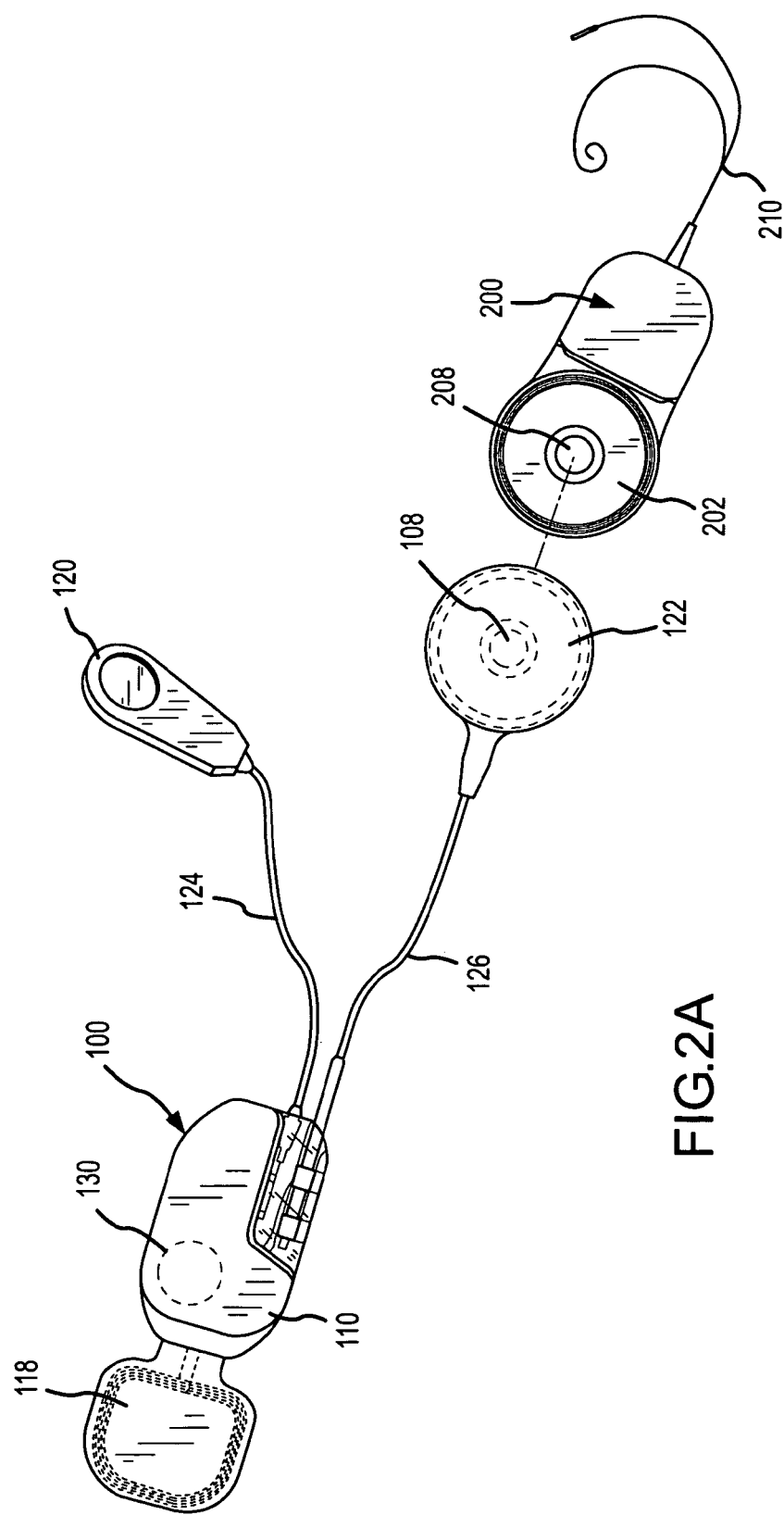
FIG. 2A illustrates an implantable portion of a cochlear implant and an implantable hearing unit.
Figure 2B:
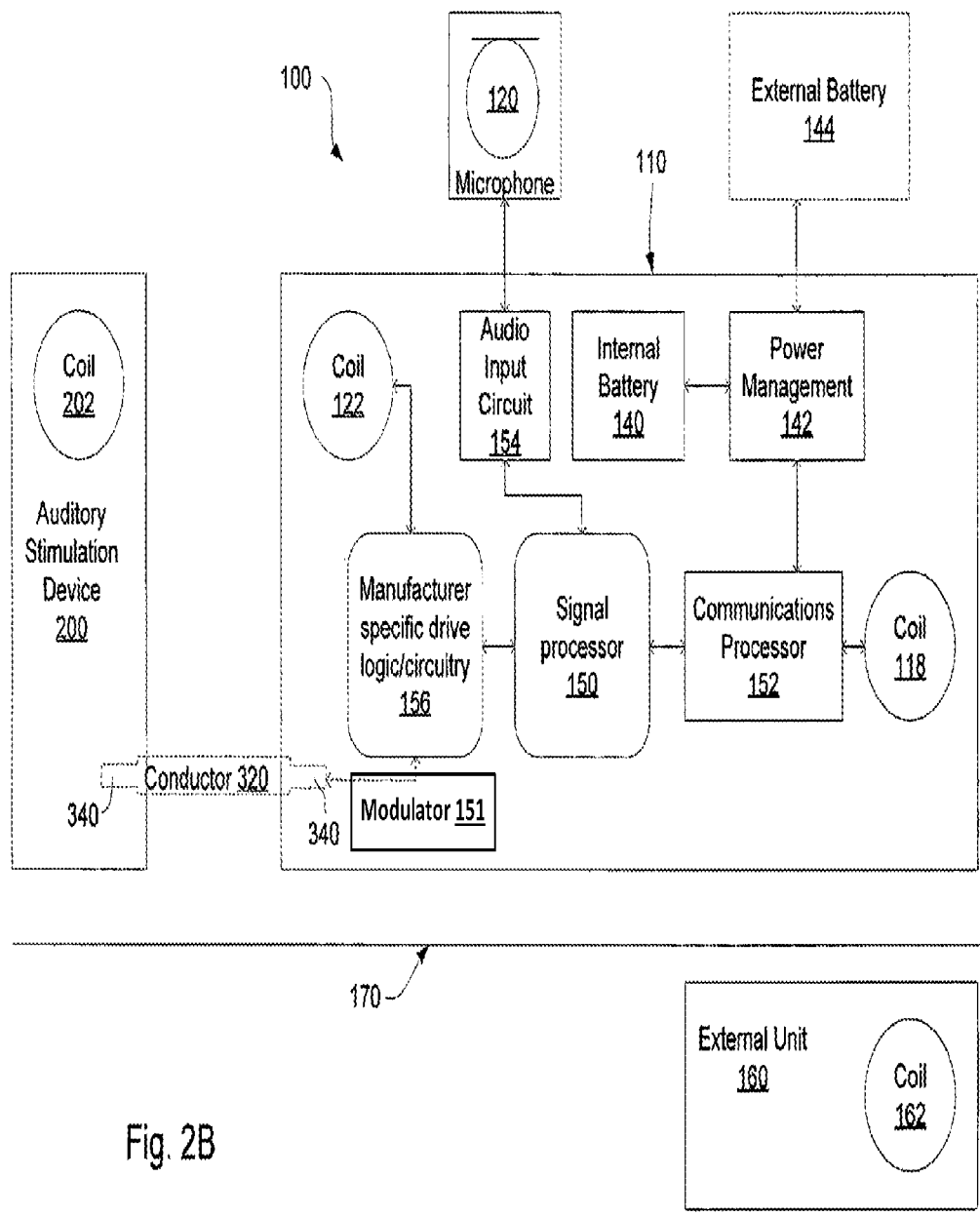
FIG. 2B illustrates a schematic diagram of the components of FIG. 2A.
Figure 3:
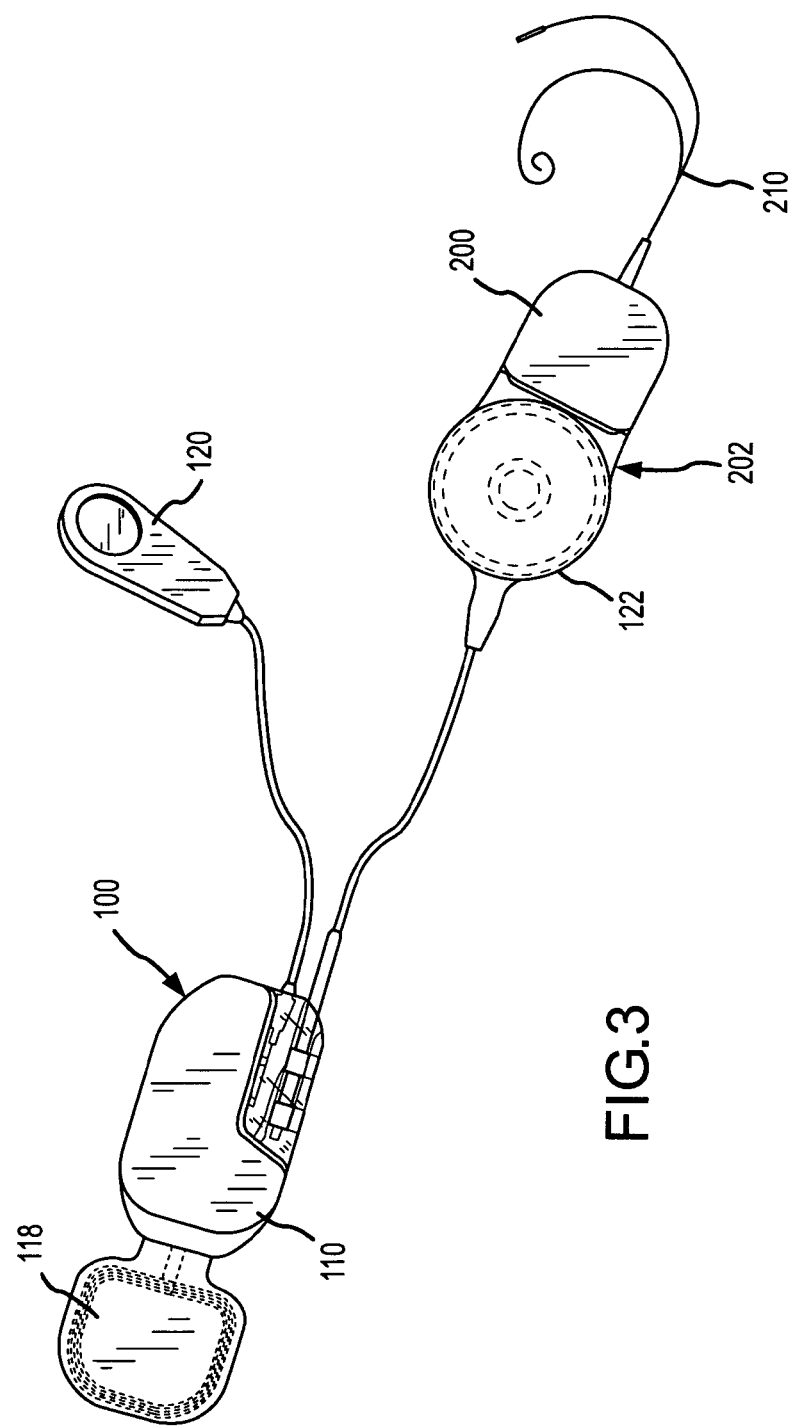
FIG. 3 illustrates the implantable portion of the cochlear implant and the implantable hearing unit of FIG. 2 in an overlying relationship.

FIGS. 1-3 illustrate one application of the present invention. As illustrated, a first application is directed to converting an existing semi-implantable hearing instrument into a fully implantable system. However, certain aspects of the present application have application beyond conversion of a semi-implantable hearing system into a fully implantable system. For instance, certain aspects may be utilized with originally manufactured implantable hearing instruments. It will be further noted that though the invention is shown in use for converting a semi-implantable cochlear implant into a fully implantable cochlear implant, the present invention may be employed in conjunction with other semi-implantable hearing instruments as well as, including, without limitation auditory brain stem stimulation systems, auditory nerve stimulation systems, and middle ear transducer systems. In this regard, the present invention has applicability with electrical stimulation systems as well as mechanical stimulation systems. Auditory stimulation devices that may be utilized with aspects of the present invention include those discussed in U.S. Pat. Nos. 5,545,219, 5,624,376 5,277,694, 5,913,376, 5,984,859, 6,315,710, 6,491,622, 6,517,476, 6,575,894, 6,676,592 and 6,726,618 the contents of which are incorporated by reference herein. Therefore, the illustrated application is for purposes of illustration and not limitation.

Generally, there are three main parts of the cochlear implant. There is an implant receiver/stimulator 200 that is implanted on a patient's skull, an electrode array 210 that extends from the housing of the receiver/stimulator 200 into the cochlea 250, and an external speech processing unit 220. See FIG. 1. One exemplary receiver/stimulator is the Nucleus made by Cochlear Limited of Australia. The external speech processing unit may comprise one or more parts depending upon the cochlear implant. For instance, the external speech processing unit may be an integrated behind the ear unit that includes a microphone, a speech processor, a transmitting coil, and a power source (e.g., batteries). Alternatively, the external speech processing unit may include a wearable processing unit/power unit 220 that is connected (e.g., wired) to a behind the ear unit 224. Such a behind the ear unit will typically include a microphone 226, a transmitting coil 228 and one or more magnets for retentive positioning with the receiver/stimulator 200. Such a separate processing unit/power unit 220 may be interconnected to patients' clothes, belt, etc.

In any case, the microphone 226 worn behind the patient's ear performs the function of the outer ear. That is, the microphone 226 picks up ambient sounds for processing. As noted, the speech processor may be mounted behind the ear or worn externally (e.g., on a belt or in a pocket etc). The speech processor, based on previous fittings selects the sounds most useful for understanding speech and codes them electronically. The electronic codes or drive signals are sent back to the transmitting coil 228, which is generally located behind or beneath the microphone 226. The transmitting coil 228 is held in place by two magnets, one located under the skin near the receiver/stimulator 200 and the other in the center of the behind the ear unit 224. The transmitting coil 228 sends the drive signals through the skin via inductive coupling to a receiving coil 202 of the implanted receiver/stimulator 200. The receiver/stimulator 200 converts the drive signals it receives into electrical signals that it sends along the electrode array 210, which is implanted in the cochlea 250 of the user.

The electrode array 210 generally consists of a plurality of small electrode bands (e.g., 24) arranged in a row inside an a flexible extension. Each individual electrode has a wire connecting it to the receiver/stimulator; each has been separately programmed to deliver electrical signals representing sounds that can vary in loudness and pitch. When the electrodes receive an electrical signal, they stimulate the appropriate populations of auditory nerve fibers, which send the messages to the brain. One advantage of such a multi-channel cochlear implant is that speech can be filtered into frequency bands by the speech processor and delivered to different points along the cochlea. Generally, the more electrodes (i.e., channels) included within the array, the better resulting sound quality a user can expect.

The cochlea is organized so that different sound frequencies preferentially stimulate different hair cells. (As the membrane along the bottom of the cochlea resonates in time with the sound vibration, hair cells at different positions along the membrane are stimulated.) Stimulating hairs located at the base of the cochlea produces perceptions of high-pitched sounds; stimulating hairs located at the opposite end (apex) of the cochlea produces perceptions of lower-pitched sounds. Accordingly, the cochlear implant has a number of electrodes at different positions on the cochlea and is designed to deliver stimuli to appropriate electrodes so that high-pitched sounds cause electrodes to stimulate hair cells towards the base of the cochlea and low-pitched sounds cause electrodes to stimulate hair cells towards the apex of the cochlea.

FIGS. 2A and 2B, illustrate an implantable hearing unit 100 that may be utilized with the receiver/stimulator 200 of the semi-implantable cochlear implant of FIG. 1 to create a fully implantable hearing instrument. As shown, the implantable hearing unit 100 includes a biocompatible implant housing 110 that is adapted to be located subcutaneously on a patient's skull. The hearing unit 100 includes a first receiving coil 118, a second transmitting coil 122, a signal processor 150 (e.g., disposed within the housing 100) and a microphone 120. It will be appreciated that each coil 118 and 122 is capable of inductively transmitting and receiving signals and that the terms 'receiving coil' and 'transmitting coil' are utilized for purposes of clarity and not by way of limitation. The receiving coil 118 is operative to transcutaneously receive electrical power and/or programming. Further, the coil 118 may provide information to an external processor. The transmitting coil 122 is operative to provide electrical power and drive signals to an implanted stimulator, as will be more fully discussed herein.

The microphone 120 is interconnected to the implant housing 110 via a communications wire 124. This allows the microphone 120 to be subcutaneously positioned to receive acoustic signals through overlying tissue. However, it will be appreciated that in other embodiments a microphone 130, as shown in phantom, may be integrated into the implant housing 110. The implant housing 110 may be utilized to house a number of components of the implantable hearing unit 100.

FIG. 2B schematically illustrates one embodiment of the internal components of the hearing unit 100 and stimulation device 200 of FIG. 2A. However, in the illustrated embodiment the implant housing 110 houses both the receiving coil 118 and the transmitting coil 122. As shown, the implantable hearing unit 100 and the stimulation device 200 are located subcutaneously beneath the skin 170 of a patient. Further, the implant housing 110 also houses a number of additional components of the hearing unit 100. Specifically, the housing 110 includes a signal processor 150, a communications processor 152, audio input circuitry 154, an internal power supply or battery 140, a power management unit 142 and manufacture specific drive logic and/or circuitry 156.

As shown, the internal battery 140 is interconnected to the power management unit 142. The power management unit 142 is operative to provide power for the implantable hearing unit as well as provide necessary rectifying functionality for use in charging the internal battery 140. Such charging utilizes transcutaneously received signals from an external unit 160, where the signals are received via the receiving coil 118. Of note, the hearing unit 100 may further incorporate one or more external batteries 144, which may be operatively interconnected to the power management unit 142. This may allow the hearing unit 100 to have a power capacity that permits uninterrupted use of the implant auditory stimulation device 200 for extended periods of time.

The audio input circuitry 154 is operative to receive an output signal from the implantable microphone 120 and provide this output signal to the signal processor 150. The audio input circuitry 154 may perform various filtering and/or amplification processes on the microphone output signal. In any case, the signal processor 150 utilizes the received microphone output signal for use in generating a drive signal for receipt by the auditory stimulation device 200. In this regard, the signal processor 150 may utilize manufacture specific drive logic and/or circuitry to generate a drive signal that is compatible with a particular auditory stimulation device 200. Such a drive signal, as well as power from the internal battery 140 and/or an external battery 144 may then be wirelessly provided to the auditory stimulation device 200 utilizing the transmitting coil 122. Alternatively, and as will be discussed herein, the drive signals and power may be provided to the stimulation device 200 utilizing a conductor 320 that extends between the housing 110 of the hearing unit 100 and the auditory stimulation device 200.

An external unit 160, which includes a coil 162 for inductively coupling to the receiving coil 118 of the hearing unit 100, is utilized to provide energy to the hearing unit 100 for use in recharging the battery or batteries of the hearing unit 100. Further, the external unit 160 may also be operative to provide programming instructions and/or control instructions to the hearing unit 100. In this regard, a communications processor 152, which may in other embodiments be incorporated into the common processor with the signal processor 150, is operative to receive program instructions from external unit 160 as well as provide responses to the external unit 160. As may be appreciated, various additional or different processing logic and/or circuitry components may be included in the implant housing 110 as a matter of design choice.

In the embodiment of FIGS. 2A and 2B, the signal processor 150 within the implant housing 110 communicates with the implant receiver/stimulator 200 via a subcutaneous inductive link. More specifically, the transmitting coil 122 of the implantable hearing unit 100 is adapted to crate an inductive link with the receiving coil 202 of the implant receiver/stimulator 200. Specifically, the transmitting coil 122 is configured to be disposed in an overlying relationship with the receiving coil 202 of the implant receiver/stimulator 200. See FIGS. 2A and 3. In the present embodiment, the transmitting coil 122 is interconnected to the implant housing 100 via a flexible communications wire 126 to permit the transmitting coil 122 to be more easily positioned relative to the receiving coil 202 of the implant receiver/stimulator 200. Mating magnets 108, 208 may be used to position the coils 122, 202. Though shown in a direct face to face relationship, it will be appreciated that the transmitting coil 122 of the implantable hearing unit 100 and the receiving coil 202 of the implant receiver/stimulator 200 may be at least partially separated so long as they maintain an inductive link.

During normal operation, acoustic signals are received subcutaneously at the microphone 120 and the microphone provides audio signals to the implantable hearing unit 100. The signal processor 150 within the housing 110 of the implantable hearing unit 100 processes the received audio signals to provide a processed audio signal (e.g., a drive signal) for transmission to the receiver/stimulator 200 via the subcutaneous inductive link between coils 122 and 202. As will be appreciated, the implantable hearing unit 100 may utilize digital processing techniques to provide frequency shaping, amplification, compression, and other signal conditioning, including conditioning based on patient-specific fitting parameters in a manner substantially similar to an external speech processing unit (e.g., 220 of FIG. 1). The implanted receiver/stimulator 200 receives drive signals from the implantable hearing unit 100 that are substantially identical to drive signals received from the external speech processing unit 220. Accordingly, the implanted receiver/stimulator 200 converts the drive signals it receives into electrical signals that are sent to the electrode array 210, which stimulates the patient's cochlea and causes the sensation of sound.

To power the fully implantable hearing instrument system, the implantable hearing unit 100 generally utilizes an external charger unit 160 (See FIG. 2B) to recharge one or more energy storage devices/batteries 140, 144 that may be disposed within or otherwise connected to the implant housing 100. In this regard, the external charger may be configured for disposition behind the ear of the implant wearer in alignment with the receiving coil 118 of the implant housing 100. The external charger and the implant housing 100 may each include one or more magnets to facilitate retentive juxtaposed positioning. Such an external charger may provide power inductively. In another arrangement, not shown, the external unit is operative to transcutaneously transmit RF signals (e.g. electromagnetic signals) to a receiver. In this arrangement, the receiver may also include, for example, rectifying circuitry to convert a received signal into an electrical signal for use in charging the energy storage device/batteries.

As will be appreciated, the use of the inductive link between the implantable hearing unit 100 and the receiver/stimulator 200 facilitates removal of the hearing unit 100 for servicing, upgrades etc. In this regard, one drawback of cochlear implants is that once electrode array 210 is inserted into the cochlea 250, subsequent removal of the electrode array 210 may result in damage to the cochlea 250. Accordingly, by utilizing the inductive link, the implantable hearing unit 100 may be removed for servicing without disturbing the receiver/stimulator 200 and/or the electrode array 210.

Of note, the system of FIGS. 1-3 may be utilized not only in retrofit applications where a semi-implantable hearing aid is converted into a fully implantable hearing aid, but also in new hearing instrument systems where it may be desirable to have an implantable portion (e.g., hearing unit 100) that is selectively removable without disturbing a more permanently implanted device (e.g., stimulator).

Figure 4:
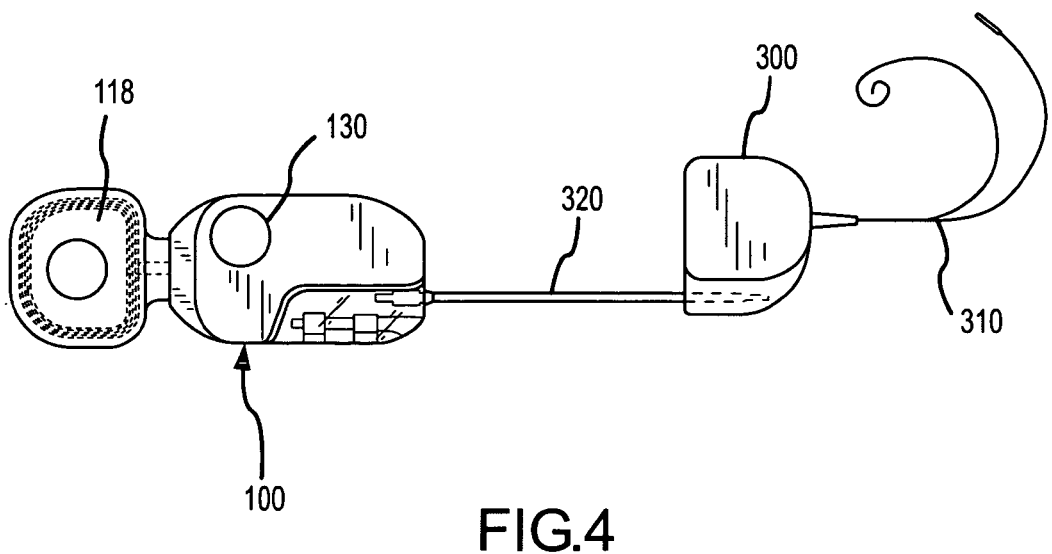
FIGS. 4 and 5 illustrate a fully implantable cochlear implant having two separate implantable modules that are interconnected with a detachable communications wire.
Figure 5:
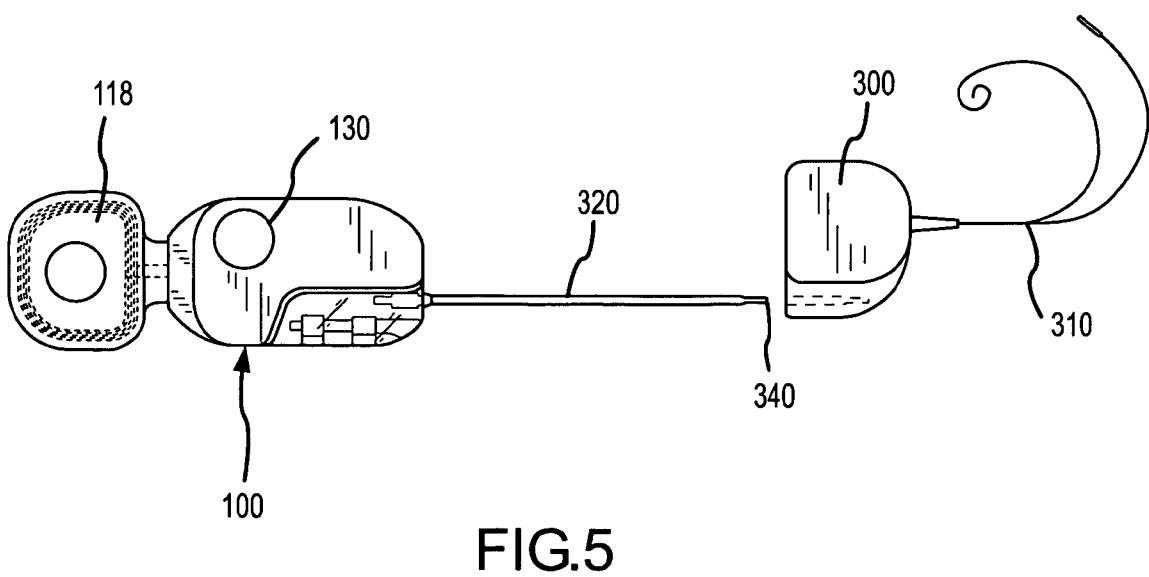

FIGS. 4 and 5 illustrate a second application of the present invention. In this application, the implantable hearing instrument system utilizes most of the same components of the implantable hearing unit 100 as discussed in relation to FIGS. 2-3 above. However, in this application the implantable hearing unit 100 is directly electrically connected to the implantable stimulator 300. Specifically, the stimulator 300 and implantable hearing unit 100 are connected via a communications wire 320 instead of by a subcutaneous inductive link. In this regard, a receiving coil is not needed for the stimulator 300 nor is a transmitting coil required for the implantable hearing unit 100. Otherwise, the structure and function of stimulator 300 is substantially the same as stimulator 200. Again, an electrode array 310 extends from the stimulator 300 and the stimulator 300 provides drive signals to the electrode array 310 is in manner that substantially unchanged in relation to that discussed above.

Though the stimulator 300 and implantable hearing unit 100 are interconnected by a communications wire 320, the communications wire 320 includes a detachable connector 340 that permits selective detachment of the communications connection between the stimulator 300 implantable hearing unit 100. In this regard, implantable hearing unit 100 may be detached from the stimulator 300 and its attached electrode array 310. As noted above, it may be undesirable after implant to remove the stimulator 300 and electrode array 310 as the potential to damage to the cochlea exists. However, it is foreseeable that one or more components of the implantable hearing unit 100 may require periodic maintenance, updating and/or replacement. For instance, while it is believed that the onboard power storage device will last for a number of years, it may eventually need to be replaced. It is further believed that advancements to hardware and/or software may become available in the future and it may be desirable to replace the entire implantable hearing unit 100 to upgrade the system. In any case, use of the detachable connector 340 in the communications wire 330 allows for such removal and/or maintenance of the hearing unit 100 without disturbing the electrode array 320.

Of note, cochlear implants typically utilize a plurality of electrodes that are each interconnected to be stimulator by an individual conductor (i.e. wire). That is, a number of wires may extend from the stimulator 300 that is equal to the number of electrodes (e.g., 22 electrodes and 22 wires) of the cochlear implant. However, it is generally undesirable to have a connector 340 that includes such a large number of conductive connections. More preferably, a communications wire 320 having fewer (e.g., two) conductors may be utilized to simplify the connector 340. A selectively detachable connector that provides at least two conductor connection and which is suited for implantation uses is described in U.S. Pat. No. 6,517,476 entitled "Connector for Implantable Hearing Aid" the contents of which are incorporated by reference herein.

In order to properly stimulate the patient's auditory system, the stimulator 300 must receive adequate information for all the electrodes or channels across the communications wire 320. Use of a two conductor wire generally requires modulating/demodulating of the signals sent from the implantable hearing unit 100 to the stimulator 300 to allow for adequate data transfer. For instance, Frequency Division Multiplexing (FDM) and Time Division Multiplexing (TDM) and or Code Division Multiplexing (CDMA) modulating/demodulating methodologies may be utilized in order to provide adequate information to the stimulator.

In any arrangement, (e.g., wireless connection or direct conductive coupling) the capacity of the power storage device(s) of the implantable hearing unit 100 will determine the length of time a user may go between necessary recharges. The capacity of a battery is generally stated in milliampere-hours, or mAh. This parameter defines the length of time the battery may deliver a given rate of current or, conversely, the maximum current deliverable over a fixed period. Although these two measures are not strictly interchangeable over all rates of discharge, they correspond well enough to permit designers to selected batteries that are sized for different applications.

It has been determined that inductive/RF transmission efficiency is a significant factor in determining time between battery charges in systems that utilize an inductive/RF power/signal link to provide power and drive signals to an implanted auditory stimulation device. The time between charges for an implantable battery connected by such a link may be calculated as:

$$T_{bc} = \frac{Q}{I_{proc} + \frac{I_{stim}}{\eta_{RF}}}. \qquad \text{Eq. 1}$$

where $T_{bc}$ is time between charges, Q is battery capacity, $I_{proc}$ is the current drain of the processor connected to the battery, $I_{stim}$ is the current drain of the auditory stimulation device driven through the link, and $\eta_{RF}$ is the efficiency of the inductive/RF link.

As an example, assume that the battery capacity is 50 mAh, current requirement for the sound processor is 1.5 mA, current requirement for a cochlear stimulator is 2.5 mA, and inductive RF link efficiency is 40%.

| | | |
|---|---|---|
| Battery capacity | 50 | mAh |
| Current drain before RF link (processor) | 1.5 | mA |
| Current drain after RF link (stimulator) | 2.5 | mA |
| RF link efficiency | 40% | |
| Resulting time between charges | 6.45 | hrs |

The RF efficiency of 40% assumed in the example above is typical of RF transmission architectures. The resulting time between charges of less than 6½ hours may be less than is desired by many users, who may prefer that a fully implantable system permit a full day of use without the inconvenience of recharging the implantable battery.

User needs may thus be compromised by the energy losses associated with inductive coupling. While the use of a conductive coupling eliminates the inefficiency of the inductive coupling, this is not an upgrade option for existing users. In this regard, the remaining option to extend the time between recharge is to increase the capacity of the battery or batteries of the implantable hearing unit 100.

Figure 6:
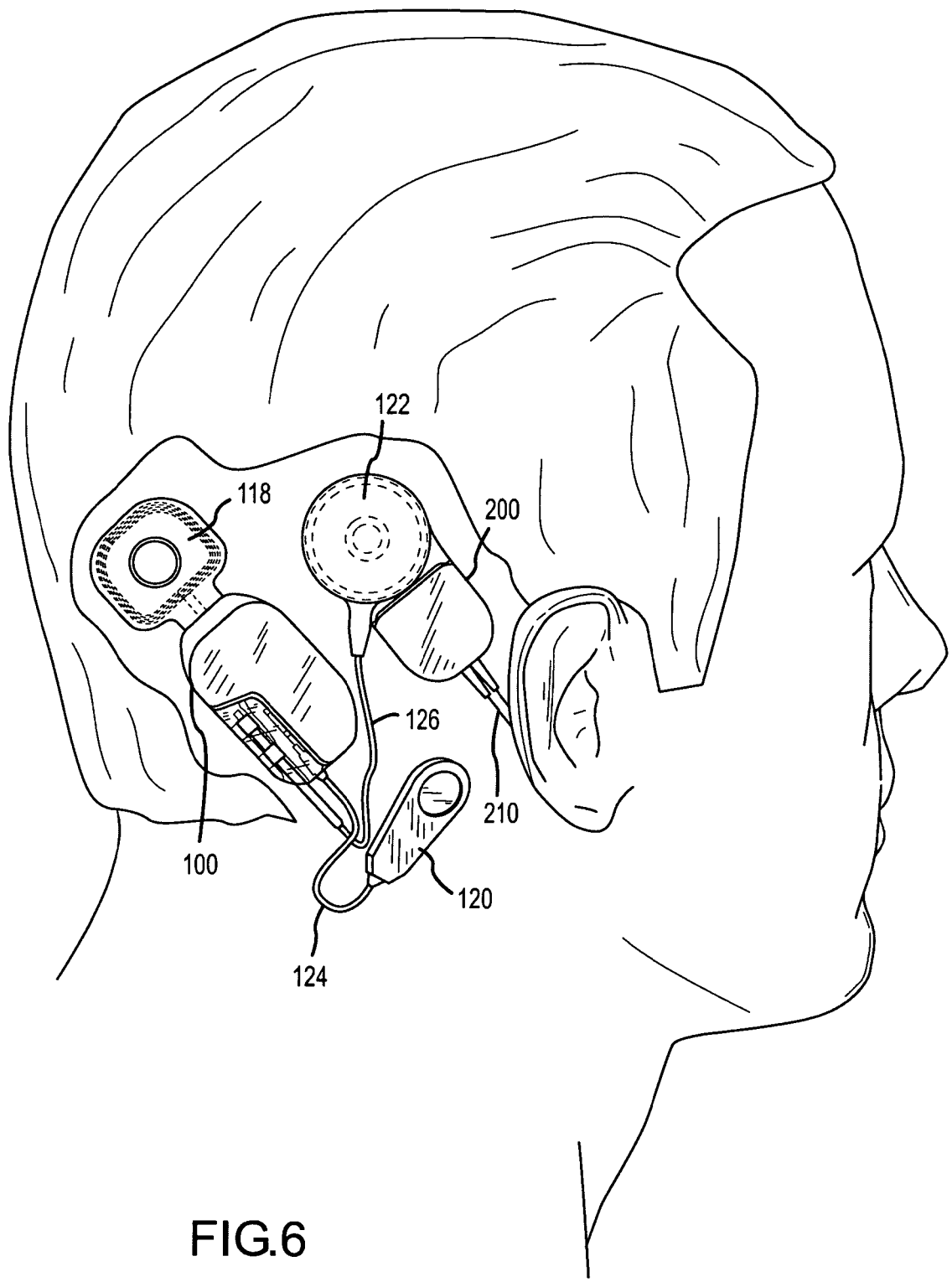
FIG. 6 illustrates a cranial placement of the components of FIG. 2A.

As shown above, the amount of battery capacity may be selected based on the type of implantable auditory stimulation device utilized and the desired time between capacity. Accordingly, for instances where low battery capacities are sufficient, a rechargeable battery 140 may be incorporated into the housing 110 of the implantable hearing unit 100. See FIG. 2B. This may result in a compact hearing unit 100. For such a compact system, a convenient location for placement of the is in the temporal region of the skull, near the typical location of the stimulator. See FIG. 6. This location minimizes the length of exposed wires 124, 126, and simplifies the surgical procedure.

In instances where greater battery capacity is required, a larger battery, or multiple batteries may be utilized. Again, a rechargeable battery or batteries may be incorporated into the housing 110 of the implantable hearing unit 100 and/or one or more separate implantable batteries 144 that are electrically connected to the implantable hearing unit 100 may be utilized. As will be appreciated, such separate implantable batteries may be detachable such that the battery or batteries may be removed and replaced without removing the implantable hearing unit 100. However, the use of larger or multiple batteries may increase the size of the implantable hearing unit making cranial location of the implantable hearing unit problematic.

In instances in which the implantable hearing unit or implantable batteries are too large for convenient placement on the skull, implantable hearing unit 100, including, for example, the receiving coil 118 and batteries may be placed subclavicularly, in a location similar to that of an implantable pacemaker. In this arrangement, the wire 124 and 126 extending between the hearing unit 100 and the microphone 120 and transmitting coil 122, respectively, may be routed subcutaneously through the soft tissues of the neck. Such an arrangement may allow for converting an existing partially implantable hearing instrument into a fully implantable hearing instrument that provides full day use (e.g., 15-16 hours) between recharges.

Those skilled in the art will appreciate variations of the above-described embodiments that fall within the scope of the invention. As a result, the invention is not limited to the specific examples and illustrations discussed above, but only by the following claims and their equivalents.

What is claimed is:

1. A method for use with an implantable stimulation system, comprising:
generating a first signal at a first supercutaneous unit, the first signal being based on a first captured signal;
transcutaneously wirelessly transmitting said first signal from said first supercutaneous unit to a second subcutaneous implant module of the implantable stimulation system, wherein the implantable stimulation system is implanted in a recipient;
activating a subcutaneously implanted stimulation device in communication with the second subcutaneous implant module to stimulate tissue of the recipient based on the transmitted first signal;
generating a second signal at a first subcutaneous implant module; and
transmitting said second signal from said first subcutaneous implant module to the second subcutaneous implant module, wherein
the implantable stimulation system includes an implanted speech processor and a component housing the implanted speech processor, and
the first subcutaneous implant module is an implantable microphone, and
one of:
the implantable microphone is spaced away from the component housing the implanted speech processor, and the implantable microphone is in signal communication with the implanted speech processor by an implanted communications wire; or
the implantable microphone is part of the component housing the implanted speech processor, and at least one of:
after transcutaneously wirelessly transmitting the first signal from the first supercutaneous unit to the second subcutaneous implant module, implanting the first subcutaneous implant module;
the generated second signal is generated by the implantable microphone; or
the transcutaneous wireless transmission occurs at a location that is subclavicularly relative to the recipient.

2. The method of claim 1, wherein:
the action of transmitting said second signal from said first subcutaneous implant module to the second subcutaneous implant module is executed wirelessly.

3. The method of claim 1, further comprising:
implanting, at a subcutaneous location, the first subcutaneous implant module after transcutaneously wirelessly transmitting the first signal from said first supercutaneous unit to the second subcutaneous implant module.

4. The method of claim 1, further comprising:
after transcutaneously wirelessly transmitting the first signal from the first supercutaneous unit to the second subcutaneous implant module, implanting the first subcutaneous implant module.

5. The method of claim 1, wherein:
transcutaneously wirelessly transmitting the first signal from the first supercutaneous unit to the second subcutaneous implant module includes transmitting the first signal from a first transmitting coil in proximity to an outer skin of a recipient of the implantable stimulation system to a subcutaneous receiving coil of the second subcutaneous implant module; and
transmitting said second signal from said first subcutaneous implant module to the second subcutaneous implant module includes transmitting the second signal to the second subcutaneous implant module while the first transmitting coil is beyond communicative range with the subcutaneous receiving coil.

6. The method of claim 1, wherein:
the action of transmitting said second signal from said first subcutaneous implant module to the second subcutaneous implant module is executed via a wired connection.

7. The method of claim 2, wherein:
transcutaneously wirelessly transmitting the first signal from the first supercutaneous unit to the second subcutaneous implant module includes transmitting the first signal from a first transmitting coil in proximity to an outer skin of a recipient of the implantable stimulation system to a subcutaneous receiving coil of the second subcutaneous implant module; and
wirelessly transmitting said second signal from said first subcutaneous implant module to the second subcutaneous implant module includes transmitting the second signal from a subcutaneous second transmitting coil of the first subcutaneous implant module to the subcutaneous receiving coil of the second subcutaneous implant module while the first transmitting coil is beyond communicative range with the subcutaneous receiving coil.

8. The method of claim 1, wherein:
the action of wirelessly transmitting occurs at a location behind and above a pinna of the recipient.

9. The method of claim 1, wherein the implantable microphone is spaced away from the component housing the implanted speech processor, and the implantable microphone is in signal communication with the implanted speech processor by an implanted communications wire.

10. The method of claim 1, wherein the implantable microphone and is part of the component housing the implanted speech processor.

11. The method of claim 1, wherein the generated second signal is generated by the implantable microphone.

12. A method for use with a fully implantable hearing prosthesis, comprising:
generating a transcutaneous wireless link between an external charging unit external to a recipient of the fully implantable hearing prosthesis and the fully implantable hearing prosthesis when implanted in the recipient, the fully implantable hearing prosthesis including an implanted microphone, an implanted speech processor, an implanted tissue stimulation device and an implanted rechargeable power storage system;
transmitting from the external charging unit to the fully implantable hearing prosthesis, using said wireless link, power to recharge the implanted rechargeable power storage system;
operating the fully implantable hearing prosthesis for at least 15 hours between recharges, and
operating at least the implanted tissue stimulation device in a manner that temporarily converts the fully implantable hearing prosthesis to a partially implantable hearing prosthesis prior to the action of operating the fully implantable hearing prosthesis for the at least 15 hours between recharges.

13. The method of claim 12, wherein:
the fully implantable hearing prosthesis is a cochlear implant.

14. The method of claim 12, further comprising:
operating the fully implantable hearing prosthesis for a full day's use between recharges.

15. The method of claim 12, wherein:
the fully implantable hearing prosthesis includes a memory and a rectifying circuit.

16. The method of claim 13, wherein:
during the action of operating the fully implantable hearing prosthesis for the at least 15 hours between recharges, the implanted rechargeable power storage system powers at least the implanted speech processor and the implanted tissue stimulation device.

17. The method of claim 12, wherein:
the implanted microphone is part of a component housing the implanted speech processor.

18. The method of claim 12, wherein:
the implanted microphone is located away from an ear canal of the recipient of the implanted microphone.

19. A method of operating a hearing prosthesis, comprising:
capturing ambient sound from external a recipient with an implanted microphone implanted in the recipient;
receiving signals from the implanted microphone with an implanted speech processor, wherein the received signals are based on the captured ambient sound;
processing the signals received from the implanted microphone, using the implanted speech processor, and outputting drive signals based on the processed signals to a stimulation device implanted in the recipient; and
evoking a hearing percept using the stimulation device based on the outputted drive signals, wherein
the hearing prosthesis includes an implanted battery implanted in the recipient, and
the method further includes, simultaneous with the action of outputting the drive signals, wirelessly transmitting power, wherein the drive signal is powered by the wirelessly transmitted power, and
the action of wirelessly transmitting occurs at a location behind and above a pinna of the recipient.

20. The method of claim 19, wherein:
the wirelessly transmitted power is received by a receiving coil of the hearing prosthesis implanted in the recipient.

21. The method of claim 19, wherein:
the implanted microphone is spaced away from a component housing the speech processor, and is in signal communication with the speech processor by an implanted communications wire.

22. The method of claim 19, wherein:
the hearing prosthesis is configured to operate solely on power from the implanted battery for at least 15 hours between recharges.

23. The method of claim 22, wherein:
the stimulation device is a cochlear implant electrode array implanted in the recipient.

24. The method of claim 19, wherein:
the wirelessly transmitted power is transmitted transcutaneously.

25. A method for use with an implantable stimulation system, comprising:
generating a first signal at a first supercutaneous unit, the first signal being based on a first captured signal;
transcutaneously wirelessly transmitting said first signal from said first supercutaneous unit to a second subcutaneous implant module of the implantable stimulation system, wherein the implantable stimulation system is implanted in a recipient;
activating a subcutaneously implanted stimulation device in communication with the second subcutaneous implant module to stimulate tissue of the recipient based on the transmitted first signal;
generating a second signal at a first subcutaneous implant module; and
transmitting said second signal from said first subcutaneous implant module to the second subcutaneous implant module, wherein
the transcutaneous wireless transmission occurs at a location that is subclavicularly relative to the recipient.

* * * * *